(12) United States Patent
Li et al.

(10) Patent No.: US 8,211,657 B2
(45) Date of Patent: Jul. 3, 2012

(54) CAPILLARY-COLUMN-BASED BIOSEPARATOR/BIOREACTOR WITH AN OPTICAL/ELECTROCHEMICAL DETECTOR FOR DETECTION OF MICROBIAL PATHOGENS

(75) Inventors: Yanbin Li, Fayetteville, AR (US); Yongcheng Liu, Blacksburg, VA (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 52 days.

(21) Appl. No.: 12/966,340

(22) Filed: Dec. 13, 2010

(65) Prior Publication Data

US 2011/0165555 A1 Jul. 7, 2011

Related U.S. Application Data

(63) Continuation of application No. 10/425,510, filed on Apr. 28, 2003, now abandoned.

(60) Provisional application No. 60/376,608, filed on Apr. 29, 2002.

(51) Int. Cl.
*G01N 31/00* (2006.01)
*G01N 33/53* (2006.01)

(52) U.S. Cl. ........ 435/7.21; 435/7.1; 436/501; 436/518; 424/9.1; 424/520; 422/50; 530/300; 530/350

(58) Field of Classification Search .................. None
See application file for complete search history.

(56) References Cited

U.S. PATENT DOCUMENTS

| | | | |
|---|---|---|---|
| 4,072,572 A | 2/1978 | Lanham et al. |
| 4,340,671 A | 7/1982 | Gibson |
| 4,525,452 A | 6/1985 | Jones et al. |
| 4,590,157 A | 5/1986 | Chandler et al. |
| 4,615,979 A | 10/1986 | Perloe |
| 4,844,869 A | 7/1989 | Glass |
| 4,918,025 A | 4/1990 | Grenner |
| 5,183,740 A | 2/1993 | Ligler et al. |
| 5,250,439 A | 10/1993 | Musho et al. |
| 5,354,661 A | 10/1994 | Doyle et al. |
| 5,447,617 A | 9/1995 | Shieh |
| 5,447,836 A | 9/1995 | Wolber et al. |
| 5,462,646 A | 10/1995 | Shieh |
| 5,496,700 A | 3/1996 | Ligler et al. |
| 5,516,409 A | 5/1996 | Kambara |
| 5,601,988 A | 2/1997 | Gordon |
| 5,624,850 A | 4/1997 | Kumar et al. |
| 5,637,467 A | 6/1997 | Meltzer |
| 5,897,993 A | 4/1999 | Sato |
| 6,001,564 A | 12/1999 | Bergeron et al. |
| 6,020,209 A | 2/2000 | Narang et al. |
| 6,177,266 B1 | 1/2001 | Krishnamurthy et al. |
| 6,245,296 B1 | 6/2001 | Ligler et al. |
| 6,274,323 B1 | 8/2001 | Bruchez et al. |
| 6,323,042 B1 | 11/2001 | Narang et al. |
| 6,375,817 B1 | 4/2002 | Taylor et al. |
| 2002/0029968 A1 | 3/2002 | Tan et al. |

FOREIGN PATENT DOCUMENTS

| | | |
|---|---|---|
| WO | 00/10584 | 3/2000 |
| WO | 00/16803 | 3/2000 |

OTHER PUBLICATIONS

Bhatia, S.K. et al., "Use of thiol-terminal silanes and heterobifunctional crosslinkers for immobilization of antibodies on silica surfaces," Anal. Biochem (1989) 178:408-413.
Boer, E.D. et al., J. Appl. Microbiol. (2000) 88:133.
Brewster, J.D. et al., "Immunoelectrochemical assays for bacteria: use of epifluorescence microscopy and rapid-scan electrochemical techniques in development of an assay for *Salmonella*," Anal. Chem. (1996) 68:4153-4159.
Buchanan, R.L. et al., "Foodborne disease significance of *Escherichia coli* O157:H7 and other enterohemorrhagic *E. coli*," Food Technol. (1997) 51:69-76.
Center for Disease Control and Prevention, "Preliminary Report: Foodborne outbreak of *Escherichia coli* O157:H7 infections from hamburgers—Western United States, 1993," Morbidity and Morality Weekly Report (Feb. 5, 1993) 42(4):85-86.
Chandler, H.M. et al., "An accelerated enzyme immunoassay for human choriogonadotropin in urine, involving reflow of specimen through capillary tubes," Clin. Chem. (1987) 33/4:498-501.
Chang, Y.H. et al., "Detection of protein A produced by *Staphylococcus auerus* with a fiber-optic-based biosensor," Biosci. Biotech. Biochem. (1996) 60(10):1571-1574.
Chapman, P.A. et al., "A comparison of immunomagnetic separation and direct culture for the isolation of verocytotoxin-producing *Escherichia coli* O157 from bovine faeces," J. Med. Microbiol. (1994) 40:424-427.
Che, Y.H. et al., "Rapid detection of *Salmonella typhimurium* in chicken carcass wash water using an immunoelectrochemical method," J. Food Prot. (2000) 63:1043-1048.
Che, Y.H. et al., "Rapid detection of *Salmonella typhimurium* using an immunoelectrochemical method coupled with immunomagnetic separation," J. Rapid Meth. Auto. Microbiol. (1999) 7:47-59.

(Continued)

*Primary Examiner* — Lisa Cook
(74) *Attorney, Agent, or Firm* — Andrus, Sceales, Starke & Sawall, LLP

(57) ABSTRACT

The present invention is directed to satisfying the need to detect microbial contamination of food products. The described bioseparator/bioreactor coupled with an optical/electrochemical biosensor was able to specifically detect *E. coli* O157:H7 from $8.8 \times 10^1$ to $8.8 \times 10^6$ CFU/ml in 2.5 hours without any enrichment. Using this invention, concentrations of S. Typhimurium ranging from $8.6 \times 10^2$ to $8.6 \times 10^6$ CFU/ml in pure culture were detected in 2 hours without any enrichment. The invention may also be used for the detection of S. Seftenberg, which has the same sensitivity as S. Typhimurium. Other pathogens such as *L. monocytogenes* and S. Heidleberg did not interfere with the detection. The optimum inner diameter of the 25 cm long column for the detection of *E. coli* O157:H7 is 250 µm. The detection limit for other microbial pathogens may be controlled by changing the length of capillary columns, using higher concentration of the labeled antibodies, altering the flow rate and concentration of the substrate, and increasing the reaction temperature to 37° C.

20 Claims, 13 Drawing Sheets

OTHER PUBLICATIONS

Colquhoun, K.O. et al., "Detection of *Escherichia coli* in potable water using direct impedance technology," J. Appl. Bacteriol. (1995) 79:635-639.

Cudjoe, K.S. et al., "Immunomagnetic separation of *Salmonella* from foods and their detection using immunomagnetic particle (IMP)-ELISA," J. Food Microbiol. (1995) 27:11-25.

Dupont, J.D. et al., "Rapid estimation of *Escherichia coli* in live marine bivalve shellfish using automated conductance measurement," J. Appl. Bacteriol. (1996) 80:81-90.

Food Safety and Inspection Service, United States Department of Agriculture, "Recall Notification Report 041-99 (regarding chorizo)" (Aug. 26, 1999, Expanded Sep. 3, 1999) 3 pages.

Fratamico, P.M. et al., "Detection of *Escherichia coli* O157:H7 by multiplex PCR," J. Clin. Microbiol. (1995) 33 (8):2188-2191.

Fratamico, P.M. et al., "Evaluation of an enzyme-linked immunosorbent assay, direct immunofluorescent filter technique, and multiplex polymerase chain reaction for detection of *Escherichia coli* O157:H7 seeded in beef carcass wash water," J. Food Prot. (1998) 61:934-938.

Gau, J. et al., "A MEMS based amperometric detector for *E. coli* bacteria using self-assembled monolayers," Biosens. Bioelectron. (2001) 16:745-755.

Gooding, C.M. et al., "Rapid and sensitive immunomagnetic separation-polymerase chain reaction for the detection of *Escherichia coli* O157:H7 in raw milk and ice-cream," J. Dairy Research (1997) 64:87-93.

Griffin, P.M. et al., "The epidemiology of infections caused by *Escherichia coli* O157:H7, other enterohemorrhagic *E. coli*, and the associated hemolytic uremic syndrome," Epidemiol. Rev. (1991) 13:60-98.

Griffiths, M.W., "Applications of bioluminescence in the dairy industry," J. Dairy Sci. (1993) 76:3118-3125.

Griffiths, M.W., "Rapid microbiological methods with hazard analysis critical control point," J.AOAC Int. (1997) 80:1143-1150.

Johnson, R.P. et al., "Detection of *Escherichia coli* O157:H7 in meat by an enzyme-linked immunosorbent assay, EHEC-Tek," Appl. Environ. Microbiol. (1995) 61:386-388.

Karch, H.C. et al., "Isolation of enterohemorrhagic *Escherichia coli* O157 strains from patients with hemolytic-uremic syndrome by using immunomagnetic separation, DNA-based methods, and direct culture," J. Clin. Microbiol. (1996) 34:516-519.

Ligler, F.S. et al., "Integrating waveguide biosensor," Anal. Chem. (2002) 74:713-719.

Liu, Y. et al., "Application of capillary column bioseparator/bioreactor to detection of *E. coli* O157:H7," Paper No. 17050, 2001 ASAE International Meeting, Sacramento, California, Jul. 30-Aug. 1, 2001, 28 pages.

Liu, Y. et al., "An antibody-immobilized capillary column as a bioseparator/bioreactor for detection of *Escherichia coli* O157:H7 with absorbance measurement," Anal. Chem. (2001) 73(21):5180-5183.

McKillip, J.L. et al., "A comparison of methods for the detection of *Escherichia coli* O157:H7 from artificially-contaminated dairy products using PCR," J. Appl. Microbiol. (2000) 89:49-55.

McKillip, J.L. et al., J. Food Prot. (2000) 63:855.

Meer, R.R. et al., "Immunochemical detection methods for *Salmonella* spp., *Escherichia coli* O157:H7 and *Listeria monocytogenes* in foods," Reviews of Environmental Contamination and Toxicology (1995) 142:1-12.

Micallef, J. et al., "Immunoassay development," Chapter 3 of Laboratory Analysis and Clinical Applications, edited by J.P. Gosling and L.V. Basso, Butterworth Heinemann, London, UK (1994) 51-68.

Miller, F., "Biosensors promise rapid detection of pathogens," Northwest Arkansas Times (Apr. 21, 2002) 1.

Miller, F., "Biosensors help detect food pathogens," DeWitt Era-Enterprise (Apr. 25, 2002) 1 page.

Nagainis, P.A. et al., "A rapid quantitative capillary tube enzyme immunoassay for human chorionic gonadotropin in urine," Clinica Chimica Acta (1986) 160:273-279.

Narang, U. et al., "A displacement flow immunosensor for explosive detection using microcapillaries," Anal. Chem. (1997) 69:2779-2785.

Padhye, N.V. et al., "Rapid procedure for detecting enterohaemorrhagic *Escherichia coli* O157:H7 in food," Appl. Environ. Microbiol. (1991) 57:2693-2698.

Palmer, C.J. et al., Appl. Environ. Microbiol. (1993) 59:786.

Park, I. et al., "Thiolated *Salmonella* antibody immobilization onto the gold surface of piezoelectric quartz crystal," Biosensors & Bioelectronics (1998) 13:1091-1097.

Poole, C.F. et al., Chromatography Today, Chapter 4, Elsevier Science: New York, NY (1991) 311-544.

Restaino, L. et al., "Antibody-direct epifluorescent filter technique and immunomagnetic separation for 10-h screening and 24-h confirmation of *Escherichia coli* O157:H7 in beef," J. Food Prot. (1996) 59:1072-1075.

Restaino, L. et al., "10-h screening and 24-h confirmation procedure for detecting *Escherichia coli* O157:H7 in beef using direct fluorescence microscopy and immunomagnetic separation," Lett. Appl. Microbiol. (1997) 24:401-404.

Ruan, C. et al., "Detection of zeptomolar concentrations of alkaline phosphatase based on a tyrosinase and horse-radish peroxidase bienzyme biosensor," Talanta (2000) 54:1095-1103.

Seo, K.H. et al., "Immunomagnetic separation and flow cytometry for rapid detection of *Escherichia coli* O157:H7," J. Food Prot. (1998) 61:812-816.

Seo, K.H. et al., J. Food Prot. (1999) 62:431.

Shekarchi, I.C. et al., "Capillary enzyme immunoassay for rapid detection of herpes simplex virus in clinical specimens," J. Clin. Microbiol. (1987) 25(2):320-322.

Sportsman, J.R. et al., "Chromatographic properties of silica-immobilized antibodies," Anal. Chem. (1980) 52:2013-2018.

Thompson, R.Q. et al., "Comparison of methods for following alkaline phosphatase catalysis: spectrophotometric versus amperometric detection," Anal. Biochem. (1991) 192:90-96.

Van Der Zee et al., J. AOAC Int. (1997) 80:934.

Vasavada, P.C., "Advances in pathogen detection," Food Testing and Analysis (1997) 47:18-20, 22-23, 47.

Wilkinson, S.L., "Eating safely in a dirty world," C&EN News (1997) 75:24-33.

Woody, J-M et al., "Comparison of the Difco EZ Coli rapid detection system and Petrifilm test kit-HEC for detection of *Escherichia coli* O157:H7 in fresh and frozen ground beef," J. Food Prot. (1998) 61:110-112.

Yang, Z.P. et al., "Immunoelectrochemical assay in combination with homogenous enzyme-labeled antibody conjugation for rapid detection of *Salmonella*," Electroanalysis (1998) 10:913-916.

Zhang, Z.Y. et al., "Capillary column-based bioseparator/bioreactor coupled with an electrochemical biosensor for detection of *Escherichia coli* O157:H7," Anal. Chim. Acta., submitted 2002.

United States Office Action for U.S. Appl. No. 10/425,510 dated Apr. 28, 2005 (16 pages).

United States Office Action for U.S. Appl. No. 10/425,510 dated Aug. 8, 2006 (20 pages).

United States Office Action for U.S. Appl. No. 10/425,510 dated Jan. 24, 2007 (16 pages).

United States Office Action for U.S. Appl. No. 10/425,510 dated Jun. 28, 2007 (27 pages).

United States Office Action for U.S. Appl. No. 10/425,510 dated Jan. 11, 2008 (28 pages).

United States Office Action for U.S. Appl. No. 10/425,510 dated Jun. 18, 2008 (32 pages).

United States Supplemental Appeal Brief for U.S. Appl. No. 10/425,510 dated Apr. 13, 2009 (28 pages).

United States Examiner's Answer to Appeal Brief for U.S. Appl. No. 10/425,510 dated Sep. 2, 2009 (41 pages).

United States Reply Brief for U.S. Appl. No. 10/425,510 dated Nov. 2, 2009 (22 pages).

United States BPAI Decision—Examiner Affirmed for U.S. Appl. No. 10/425,510 dated Oct. 12, 2010 (18 pages).

CAPILLARY-COLUMN-BASED BIOSEPARATOR/BIOREACTOR WITH AN OPTICAL/ELECTROCHEMICAL DETECTOR FOR DETECTION OF MICROBIAL PATHOGENS

CROSS-REFERENCE TO RELATED APPLICATIONS

The present application is a Continuation of U.S. patent application Ser. No. 10/425,510, filed Apr. 28, 2003 now abandoned, which claims the benefit of U.S. Provisional Application No. 60/376,608, filed Apr. 29, 2002, which is incorporated herein by reference.

STATEMENT REGARDING FEDERALLY SPONSORED RESEARCH OR DEVELOPMENT

This invention was made with Government support under the terms of Grant Nos. 2001-35201-10056 and 2001-34211-10288 awarded by the USDA/NRI and USDA/FSC. The Government has certain rights in this invention.

BACKGROUND OF THE INVENTION

1. Field of the Invention

The present invention relates to a highly sensitive and convenient method using a capillary column as a bioseparator/bioreactor for detection of microbial contamination in food products.

2. Brief Description of the Related Art

Microbial contamination in food products is a major concern to the food industry, regulatory agencies and consumers [S. L. Wilkinson, C and CE News. 75 (1997) 24]. Foodborne illness caused by pathogenic microorganisms poses a serious threat to public health. The Center for Disease Control and Prevention (CDC) estimated that annually 76 million illnesses, 325,000 hospitalized and 5,000 deaths were caused by bacterial contamination of food products in the United States. It is imperative to develop more effective and rapid technology to detect specific pathogens such as *Escherichia coli* O157:H7, *Salmonella* Typhimurium and *Listeria monocytogenes* to ensure that safe food products reach the public [M. W. Griffiths, J. AOAC Int. 80 (1997) 1143] [H. Van der Zee, et al., J. AOAC Int. 80 (1997) 934] [P. C. Vasavada, Food Testing and Analysis. 47 (1997) 18]. *Escherichia coli* O157:H7 is one of the most dangerous pathogens [R. L. Buchanan, et al., Food Technol. 51 (1997) 69] [P. M. Griffin, et al., Epidemiol. Rev. 13 (1991) 60], and it has been associated with two important human diseases: hemorrhagic colitis and hemolytic uremic syndrome (HUS). It can be transmitted via contaminated foods such as raw ground beef and unpasteurized milk [Center of Disease Control, Morbid. Mortal. Weekly Rep. 42 (1993) 85] and from person to person [Center of Disease Control, Morbid. Mortal. Weekly Rep. 42 (1993) 85], e.g., in nursing houses and day care facilities. *Salmonella* Typhimurium, one of the pathogens most likely to be found in commonly slaughtered livestock (cattle, sheep, and swing) and poultry (chicken and turkey), causes acute diarrhea, vomiting, abdominal pain, and fever. Occasionally, it may cause blood stream infection and death. Symptoms occur 6-72 hours after eating contaminated foods [USDA Food Safety and Inspection Service (FSIS). 1999, 26 Aug.]. *Salmonella* contamination in food products also results in the large economical burden for the industry due to products recalls.

Conventional microbiological culture methods used for bacterial detection are cumbersome and time-consuming, requiring 3-4 days for confirmation. Immunosorbent assays also suffer from complexities in sample pretreatment and measuring procedures, because they use isotopes and are susceptible to interference caused by chromogens in food samples. Even though some methods have been developed in an effort to replace traditional techniques, the enzyme-linked immunosorbent assays (ELISA), which can achieve high specificity and sensitivity, still needs 24 hours or more to achieve the necessary detection limits [K. S. Cudjoe, et al., J. Food Microbiol. 27 (1995) 11].

Some methods have been developed for the rapid detection of *E. coli* O157:H7 in an effort to replace conventional techniques [E. D. Boer, et al., J. Appl. Microbiol. 88(S) (2000) 133S]. Several procedures, such as antibody direct epifluorescent filter technique [L. Restaino, et al., J. Food Prot. 59 (1996) 1072] [L. Restaino, et al., Lett. Appl. Microbiol. 24 (1997) 401], ATP bioluminescence [M. W. Griffiths, J. Dairy. Sci. 76 (1993) 3118], enzyme-linked immunosorbent assays [R. P. Johnson, et al., Appl. Environ. Microbiol. 61 (1995) 386] [P. M. Fratamico, et al., J. Food Prot. 61 (1998) 934] [J-M. Woody, et al., J. Food Prot. 61 (1998) 110] [N. V. Padhye, et al., Appl. Environ. Microbiol. 57 (1991) 2693], impedance [J. Dupont, et al., J. Appl. Bacteriol. 80 (1996) 81] [K. O. Colquhoun, et al., J. Appl. Bacteriol. 79 (1995) 635], multiplex polymerase chain reaction [J. P. Mckillip, et al., J. Appl. Microbiol. 89 (2000) 49] [P. M. Fratafico, et al., J. Clin. Microbiol. 33 (1995) 2188] [C. M. Gooding, et al., J. Dairy Research 64 (1997) 87] [J. L. Mckillip, et al., J. Food Prot. 63 (2000) 855], and flow cytometry [K. H. Seo, et al., J. Food Prot. 61 (1998) 812], have been reported. These procedures could reduce analysis time and give presumptive results within several hours to one day, when compared with cultural plating procedures that require two or more days. The detection limit of these methods varied from $10^3$ to $10^5$ cells/ml. Since *E. coli* O157:H7 cells in foods are usually present in small numbers, pre-enrichment is necessary to obtain a detectable signal for target bacteria in applications of these methods.

Kim and Park [I. S. Park, et al., Biosens. Bioelectron. 13 (1998) 1091] developed piezoelectric biosensors for detection of *Salmonella* in the range of $9.9 \times 10^5$ to $1.8 \times 10^8$ CFU/ml. Seo et al. [K. H. Seo, et al., J. Food Prot. 62 (1999) 431] developed an integrated optic interferometer system for detection of *Salmonella* in the range of $1.0 \times 10^5$ to $1.0 \times 10^7$ CFU/ml by observing the fringe shift generated by refractive index variation. By using membrane separation and electrochemical analysis, a biosensor possessed a linear response for S. Typhimurium from $5.0 \times 10^3$ to $5.0 \times 10^6$ CFU/ml within 2 hours [Z. P. Yang, et al., Electroanalysis 10 (1998) 913]. When immunomagnetic separation and electrochemical detection were applied, a biosensor system could be able to detect S. Typhimurium from $1.0 \times 10^3$ to $1.0 \times 10^7$ [Y. H. Che, et al., J. Rapid Meth. Auto. Microbiol. 7 (1999) 47] [Y. H. Che, et al., J. Food Prot. 63 (2000) 1043]. Brewster et al. [J. D. Brewster, et al., Anal. Chem. 68 (1996) 4153] prepared immunoelectrochemical sensors for the detection of *Salmonella*. Chang et al. [Y. H. Chang, et al., Biosci. Biotechnol. Biochem. 60 (1996) 1571] constructed a compact fiber optic-based biosensor for detection of *Salmonella aureus* by measuring laser light signal at 488 nm. These methods make it possible to miniaturize immunosensors in detection of bacteria. However, each of these methods has its particular disadvantages such as high detection limit and poor specificity, high cost of instruments and materials, and/or time-consuming.

Capillary columns offer the advantage of better surface-to-volume interaction and the reduced amount of reagent. More importantly, it would take shorter time for molecules to reach the surface in a capillary, resulting in a faster assay. Capillary columns have proven to be very successful in separation techniques [C. F. Poole, et al., Chromatography Today, Elsevier Science: New York, N.Y. 1991], but there are few reports on their applications in the separation and detection of pathogens. Recently, capillary columns were used as a bioseparator/bioreactor by chemically immobilizing anti-*E. coli* O157:H7 antibodies onto the inner wall of the column [Y. Liu, et al., Anal. Chem. 73 (2001) 5180]. After a sample and alkaline-phosphatase-labeled antibodies passed through the column and the "sandwich" immunocomplexes were formed, a substrate, p-phenol phosphate was added and then the absorbance of the enzymatic products was measured. A detection limit of 500 CFU/ml was obtained.

The invention described herein comprises a flow-injection analysis system with a bienzyme biosensor used to detect the product of enzymatic reaction instead of optical measurement. Phenol produced from the enzymatic reaction between alkaline phosphatase and its substrate, phenol phosphate was detected by a tyrosinase-horseradish peroxidase biosensor. Compared to UV spectroscopy, electrochemistry provided more sensitive detection [R. Q. Thompon, et al., Anal. Biochem. 192 (1991) 90]. With optimized conditions, a detection range from $8.8 \times 10^1$ to $8.8 \times 10^6$ CFU/ml was obtained for *E. coli* O157:H7, and the assay time was less than 2.5 hours without any enrichment. Capillary column has been used as a bioseparator/bioreactor for the detection of *E. coli* O157:H7 and a detection limit of $8.8 \times 10^1$ CFU/ml was obtained [Z. Y. Zhang, et al., Anal. Chim. Acta, 2002 (submitted)] [Y. Liu, et al., Anal. Chem. 73 (2001) 5180]. The capillary immunosensor was also used to detect S. Typhimurium with a total assay time less than 2 hours without any enrichment and a detection limit of $10^2$ cfu/ml.

We demonstrate that this method is more sensitive and convenient compared to other methods developed for the detection of microbial contamination because capillary columns can offer the advantage of high surface-to-volume interaction.

References mentioned in this background section are not admitted to be prior art with respect to the present invention.

BRIEF SUMMARY OF THE INVENTION

The present invention is directed to satisfying the need to detect microbial contamination of food products. The described bioseparator/bioreactor coupled with an optical/electrochemical biosensor was able to specifically detect *E. coli* O157:H7 from $8.8 \times 10^1$ to $8.8 \times 10^6$ CFU/ml in 2.5 hours without any enrichment. Using this invention, concentrations of S. Typhimurium ranging from $8.6 \times 10^2$ to $8.6 \times 10^6$ CFU/ml in pure culture were detected in 2 hours without any enrichment. The invention may also be used for the detection of S. Seftenberg, which has the same sensitivity as S. Typhimurium. Other pathogens such as *L. monocytogenes* and S. Heidleberg did not interfere with the detection. The optimum inner diameter of the 25 cm long column for the detection of *E. coli* O157:H7 and S. Typhimurium is 250 μm. The detection limit for other microbial pathogens may be controlled by changing the length of capillary columns, using higher concentration of the labeled antibodies, altering the flow rate and concentration of the substrate, and increasing the reaction temperature to 37° C.

BRIEF DESCRIPTION OF THE DRAWINGS

These and other features, objects and advantages of the present invention will become better understood from a consideration of the following detailed description and accompanying drawings.

DETAILED DESCRIPTION OF THE INVENTION

Figure 1:
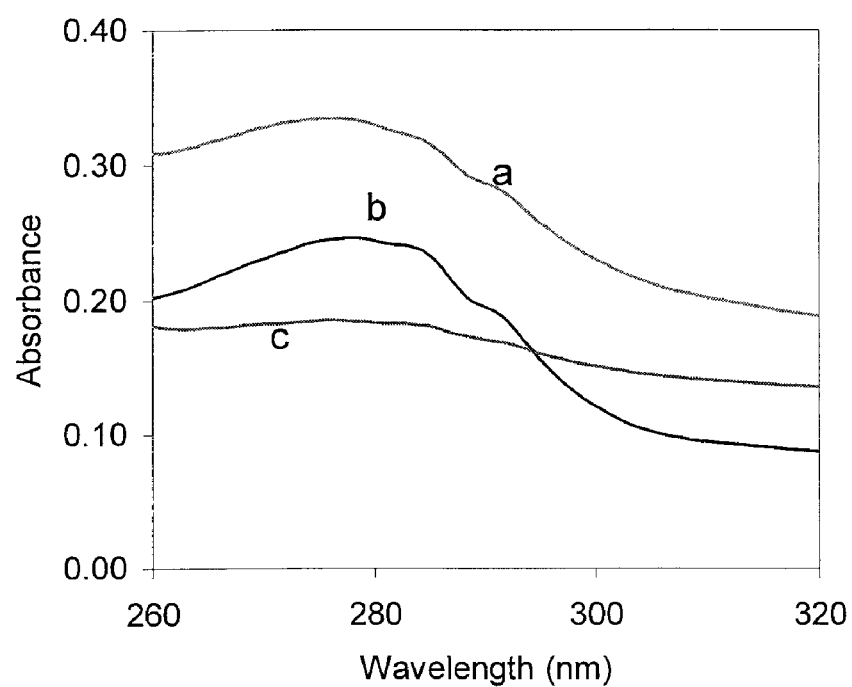
FIG. 1 shows the spectrum of anti-*Salmonella* antibody before and after the immobilization where, a is the spectrum of 0.1 mg/ml anti-*Salmonella* antibodies before immobilization, b is the spectrum of the first 0.25 ml of 0.1 mg/ml anti-*Salmonella* antibodies after being pumped through the capillary, and c is the spectrum of the second 0.25 ml of 0.1 mg/ml anti-Salmonella antibodies after being pumped through the capillary.

With reference to FIGS. 1-11, the preferred embodiment of the present invention may be described. The present invention is directed to satisfying the need to detect microbial contamination of food products. The described bioseparator/bioreactor coupled with an optical/electrochemical biosensor was able to specifically detect *E. coli* O157:H7 in 2.5 hours and S. Typhimurium in 2 hours without any enrichment.

In this invention a critical step is the immobilization of antibodies onto the capillary column. In order to determine antibody binding, atomic force microscope and surface plasma resonance have been used to monitor the antibody immobilization on a gold electrode surface [J. Gau, et al., Biosens. Bioelectron. 16 (2001) 745]. I-labeled antibodies have also been used to determine the amount of antibodies immobilized on the silica surface [S. K. Bhatia, et al., Anal. Biochem. 178 (1989) 408].

However, direct analysis of the inside surface of a 250 μm inner diameter fused silica capillary is difficult. Hence, the absorbance at 280 nm of the antibody solution before and after the immobilization was measured with the procedure described by Sportsman and Wilson [J. R. Sportsman, et al., Anal. Chem. 52 (1980) 2013] to demonstrate that the antibody was coupled onto the inner surface of capillaries.

Optimization Parameters for Immobilizing the Primary Antibodies

Concentrations of 0.6 ml of 0.1 mg/ml antibodies were pumped into columns with different lengths at a flow rate of 0.5 ml/h. The first half of the 0.3 ml and the second half of the 0.3 ml solution after the immobilization were collected at the outlet separately. The absorbance was measured at 280 nm spectrophotometrically (HP 8453 UV-Vis-spectrophotometer, HP).

Table 1 shows the absorbance data collected before and after the antibody immobilization. When 0.3 ml of antibodies was pumped into the column, the reaction ratio of antibodies increased as the column length increased. This demonstrated that the longer the column, the more volume of antibodies needed. The result also showed that for the 3 m capillary column, less than 0.6 ml of antibodies are needed for the immobilization. Therefore, 0.4 ml of 0.1 mg/ml antibodies was selected for the antibody immobilization. Considering the instrumental noise, the difference between the initial absorbance of antibodies and that of the first half of the 0.3 ml antibodies after the immobilization was negligible. Therefore, 0.6 ml of antibodies are sufficient for the antibody immobilization when the capillary length is less than 3 m.

TABLE 1

The absorbance data collected before and after the antibody immobilization and the reaction ratio for different lengths of capillary columns.

| Column Length | Before immobilization | Absorbance of antibodies After immobilization First half 0.3 ml | Second half 0.3 ml | Reaction ratio (%) |
|---|---|---|---|---|
| 30 cm | 0.1529 | 0.1240 | 0.1538 | 18.9 |
| 2 m | 0.1529 | 0.0891 | 0.1508 | 41.7 |
| 3 m | 0.1529 | 0.0385 | 0.1486 | 74.8 |

*It is based on the sample of first half 0.3 ml antibodies. The reaction ratio of antibodies was defined as the difference of absorbance before and after the antibody immobilization divided by the absorbance of antibodies before immobilization.

The procedure for the immobilization of anti-Salmonella antibodies is the same as that of anti-E. coli O157:H7 antibodies. FIG. 1 shows the spectrum for the absorbance at 280 nm of the anti-Salmonella antibodies that were pumped through the capillary column. When the first 0.25 ml of antibodies were pumped through the capillary, the absorbance decreased by approximately 30% with the absorbance of the second 0.25 ml of antibodies further reducing absorbance by approximately 20%.

For S. Typhimurium an optimal temperature for the reaction is 37° C. Under the optimum temperature, a detection limit of $8.6 \times 10^2$ CFU/ml for S. Typhimurium was obtained, which is one order of magnitude lower than that at room temperature. At the same time, the linear range from $8.6 \times 10^3$ CFU/ml to $8.6 \times 10^6$ CFU/ml for S. Typhimurium was obtained, compared to $8.6 \times 10^4$ CFU/ml to $8.6 \times 10^6$ CFU/ml under room temperature.

The Length, Diameter, and Flow Rate of the Capillary Column

Figure 2:
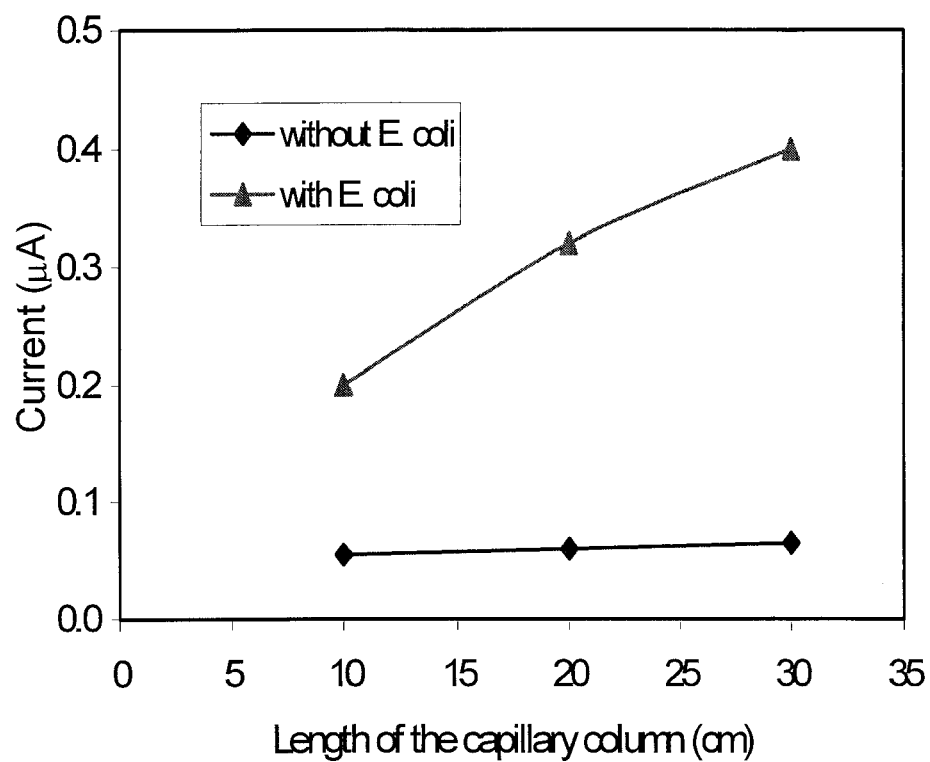
FIG. 2 shows the effect of the length of capillary columns on the peak current in the detection of *E. coli* O157:H7 in pure culture ($4.3 \times 10^5$ CFU/ml).

The length of the capillary column is an important parameter of the capillary bioseparator/bioreactor. Both a control devoid of E. coli O157:H7 and $4.3 \times 10^5$ CFU/ml E. coli O157:H7 pure culture, were analyzed at the same time to obtain sample and background signals for different lengths of the columns. FIG. 2 represents the different signals for different lengths of columns. The sample signal increased as the capillary length increased, but the background signal remained almost constant. Narang et al. [U. Narang, et la., Anal. Chem. 69 (1997) 2779] reported that the length of the capillary can be selected to achieve the limit of detection desired for a particular TNT immunoassay.

We demonstrate that changing the length of the column can alter the detection limit desired for particular concentration of bacteria. However, when the column is too long (>1 m), a larger volume of the sample is needed as well as a longer time period for antibody-antigen reaction to occur. Therefore, 25 and 40 cm long columns were selected for E. coli O157:H7 and S. Typhimurium, respectively.

Improvement of the detection limit may also be obtained through the optimization of capillary column diameter. The 25 cm long columns with 99, 152, 250, 325, and 525 μm inner diameter were tested to optimize the capillary diameter based on the ratio of the signal-to-background. Both a control devoid of E. coli O157:H7 and $8.8 \times 10^5$ CFU/ml E. coli O157:H7 pure culture were used to obtain signals from the column.

Figure 3:
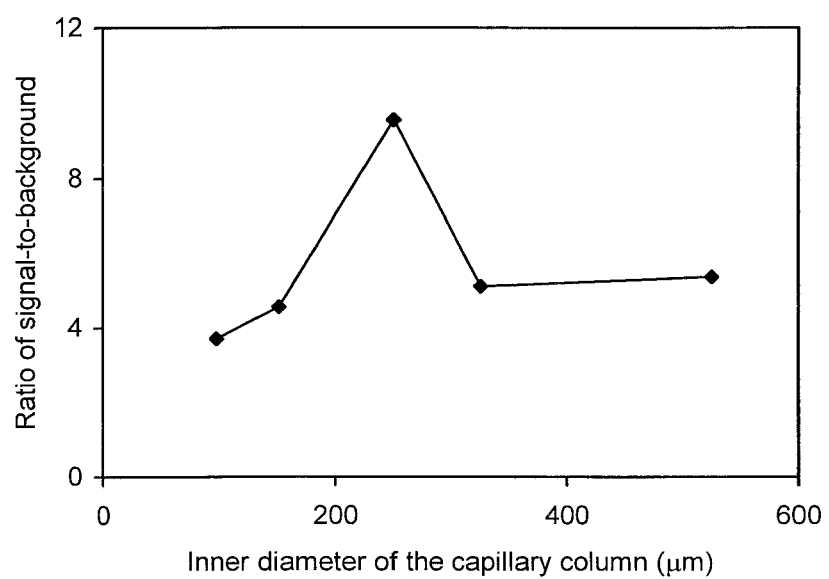
FIG. 3 shows the effect of the inner diameter of columns on the ratio of the signal-to-background.

FIG. 3 shows the effect of the inner diameter of columns on the ratio of the signal-to-background. As is shown in FIG. 3, 250 μm inner diameter is the optimal for the highest ratio of the signal-to-background, when the sample was pumped through the column at a flow rate of 0.5 ml/h. Therefore, at 0.5 ml/h flow rate, the linear flow velocity of 99, 152, 250, 325, and 525 μm inner diameter columns is 65, 28, 10, 6, and 3 ml/h mm$^2$, respectively. A 10 ml/h mm$^2$ linear flow velocity resulted in the highest ratio of the signal-to-background.

For each antigen-antibody pair, there is an optimum flow rate, which is related to the dissociation constant of antibodies [U. Narang, et al., Anal. Chem. 69 (1997) 2779]. Increasing the flow rate above this level may cause decreased antibody-antigen interaction time. Decreasing the flow rate too much may result in poor discrimination of the sample signal from the high background caused by nonspecific bounding in the capillary column. Thus, for columns with different diameters, linear flow velocity (=flow rate/cross-sectional area of the capillary) is a more accurate measurement for comparing the flow streams through the column.

Figure 4:
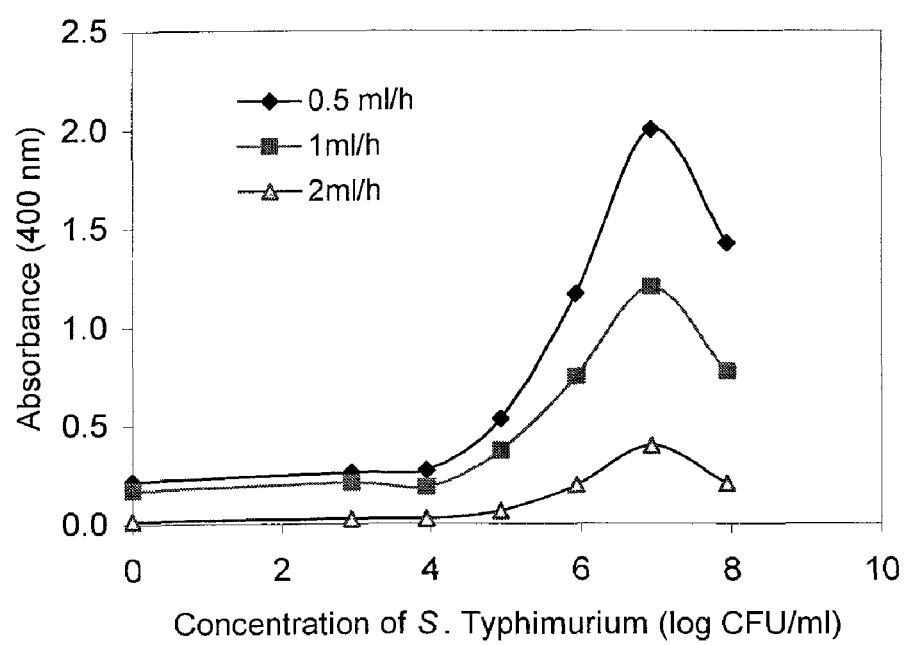
FIG. 4 shows the effect of the flow rate of substrates on the absorbance of 4-nitrophenol.

For enzymatic reactions, the flow rate of substrates had an effect on the peak current and on the detection limit. Therefore, for detection of E. coli O157:H7, a flow rate of 0.5 ml/h was used. For S. Typhimurium samples, FIG. 4 shows the effect of the flow rate of the substrate on the absorbance, indicating that the higher the flow rate, the lower the signal. To detect concentrations as low as $8.6 \times 10^2$ CFU/ml of S. Typhimurium a flow rate of 2 ml/h or 1.5 ml/h was used, but if the flow rate was increased to 3 ml/h, the detection limit was $8.6 \times 10^3$ CFU/ml. Hence, for detection of S. Typhimurium the optimum substrate flow was selected at 2 ml/h.

For E. coli O157:H7, the optimum contents of the substrate solutions were determined to be $1.0 \times 10^{-3}$ M phenyl phosphate disodium and $1.0 \times 10^{-2}$ M MgCl$_2$ in pH 10, 0.1 M Tris buffer [C. M. Gooding, et al., J. Dairy Research 64 (1997) 87]. For S. Typhimurium, pH 9.0 Tris buffer is the best media for the enzymatic reaction and the maximum absorbance of 4-nitrophenol from the enzymatic reaction was observed at $1.0 \times 10^{-2}$ M MgCl$_2$.

Figure 5:
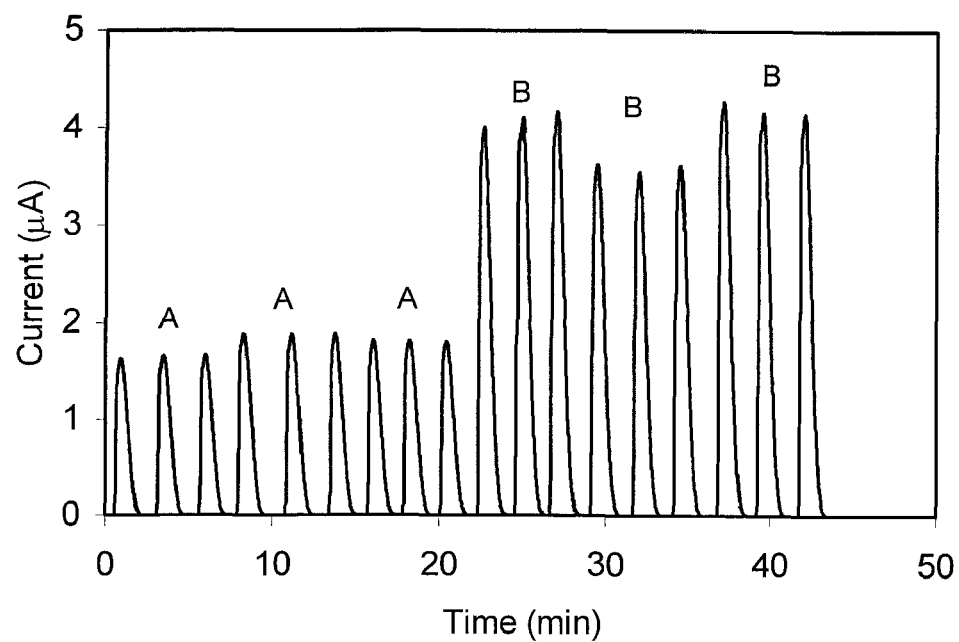
FIG. 5 shows column-to-column reproducibility wherein A is $4.6 \times 10^5$ CFU/ml *E. coli* O157:H7 and B is $4.6 \times 10^6$ CFU/ml *E. coli* O157:H7 of sample.

In order to evaluate batch procedures, six 30 cm long capillary columns (250 μm i.d.) were coated with antibodies simultaneously. Three columns were pumped with 0.5 ml of $4.6\times10^5$ CFU/ml E. coli O157:H7 sample and three columns were pumped with 0.5 ml of $4.6\times10^6$ CFU/ml E. coli O157:H7 sample at a flow rate of 0.5 ml/h. The relative standard deviation (RSD) obtained by the six columns was 7.27% for the $4.6\times10^6$ CFU/ml E. coli O157:H7 sample, and 6.23% for the $4.6\times10^5$ CFU/ml E. coli O157:H7 sample, indicating reproducibility using a batch method. FIG. 5 shows column-to-column reproducibility using batch methods (three injections were made to get the current response for each column).

Concentration of Antibodies

Figure 6:
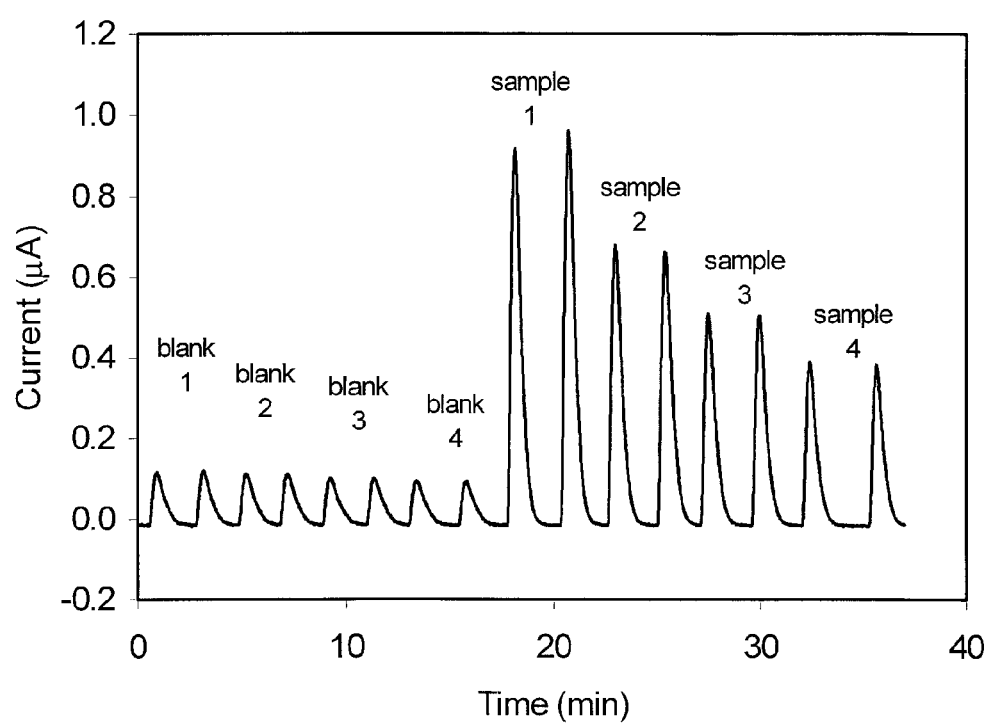
FIG. 6 shows the effect of the concentrations of AP labeled anti-*E. coli* O157:H7 antibodies on the peak current measurement with and without *E. coli* O157:H7 in pure culture ($8.8 \times 10^5$ CFU/ml). The concentrations of labeled anti-*E. coli* O157:H7 antibodies are: sample 1 and blank 1: 2.0 mg/l; sample 2 and blank 2: 1.0 mg/l; sample 3 and blank 3: 0.5 mg/l; sample 4 and blank 4: 0.25 mg/l.

The concentration of labeled antibodies also has effect on the ratio of signal-to-background and that the ratio of signal-to-background increased as the concentration of labeled antibodies increased [J. Dupont, et al., J. Appl. Bacteriol. 80 (1996) 81]. In order to test the effect of the concentration of AP-labeled anti-E. coli 0157:H7 antibodies on the peak current measurement, 50 μl of AP-labeled anti-E. coli O157:H7 antibodies at different concentrations from 0.25 mg/l to 2.0 mg/l were used. A control devoid of E. coli O157:H7 and $8.8\times10^5$ CFU/ml E. coli O157:H7 pure culture were conducted at the same time. FIG. 6 shows that the response to E. coli O157:H7 increased as the amount of the AP-labeled anti-E. coli O157:H7 antibodies increased, and the background did not change significantly. When the concentration of the labeled antibody was under 1 mg/l, the ratio of the signal-to-background was very small, therefore, 1 mg/l of AP-labeled anti-E. coli O157:H7 antibodies was selected. At least 12 μl solution was needed to fill the column (length=25 cm, i.d.=250 μm), therefore, the volume of 50 μl AP-labeled anti-E. coli O157:H7 antibodies was used. For S. Typhimurium, 100 μl of 2 mg/ml Salmonella labeled antibodies were selected to increase the ratio of signal-to-background for the detection. Using these parameters, concentrations as low as $8.8\times10^2$ CFU/ml S. Typhimurium could be detected.

Electrochemical Detection of Enzyme Labels

The sensitivity of an enzyme immunoassay is usually controlled by the sensitivity of the method used to detect the enzyme label. The enzyme label can be readily detected through the conversion of a substrate into a product, either using an optical method such as UV absorbance, fluorescence and luminescence, or by an electrochemical method. Electrochemical methods, especially electrochemical biosensors, have a very high sensitivity for the detection of alkaline phosphatase. In addition, electrochemical biosensors may be used to detect the binding of nanocrystals. Nanocrystals may be used to label antigen marker agents and the binding to the antigen marker agents can be determined by determining the level of binding of the nanocrystals using standard techniques known to those of skill in the art. Thus, nanocrystals may be used as detectable markers.

Recently, a bienzyme electrochemical biosensor based on tyrosinase and horseradish was developed and applied to the detection of zeptomolar concentrations of alkaline phosphatase in a flow injection system [C. Ruan, et al., Talanta 54 (2000) 1095]. The enhanced sensitivity of the bienzyme biosensor for detection of alkaline phosphatase was observed in comparison with its corresponding mono-enzyme biosensor.

The bienzyme biosensor was used to detect the enzyme label bound onto the capillary column through E. coli O157:H7. The enzyme labels catalyzed the hydrolysis of substrate, and produced phenol, which was detected by the bienzyme biosensor. The optimum contents of the substrate solutions were determined to be $1.0\times10^{-3}$ M. phenyl phosphate disodium and $1.0\times10^{-2}$ M $MgCl_2$ in pH 9.0, 0.1 M Tris buffer at an optimum flow rate of 2 ml/h. The pH of the substrate had great influence on the enzymatic reaction. The peak current was much higher for the substrate in basic solutions than that in neutral or acidic solutions.

Figure 7A:
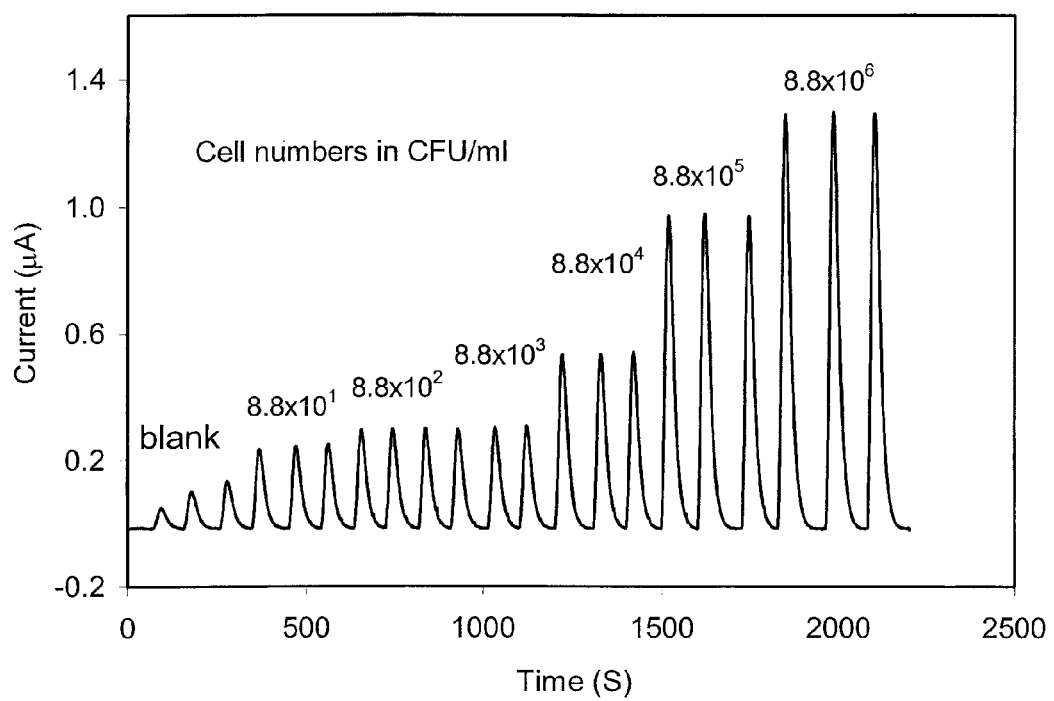
FIG. 7A shows the electrochemical signals for samples containing *E. coli* O157:H7 from blank to $8.8 \times 10^6$ CFU/ml.
Figure 7B:
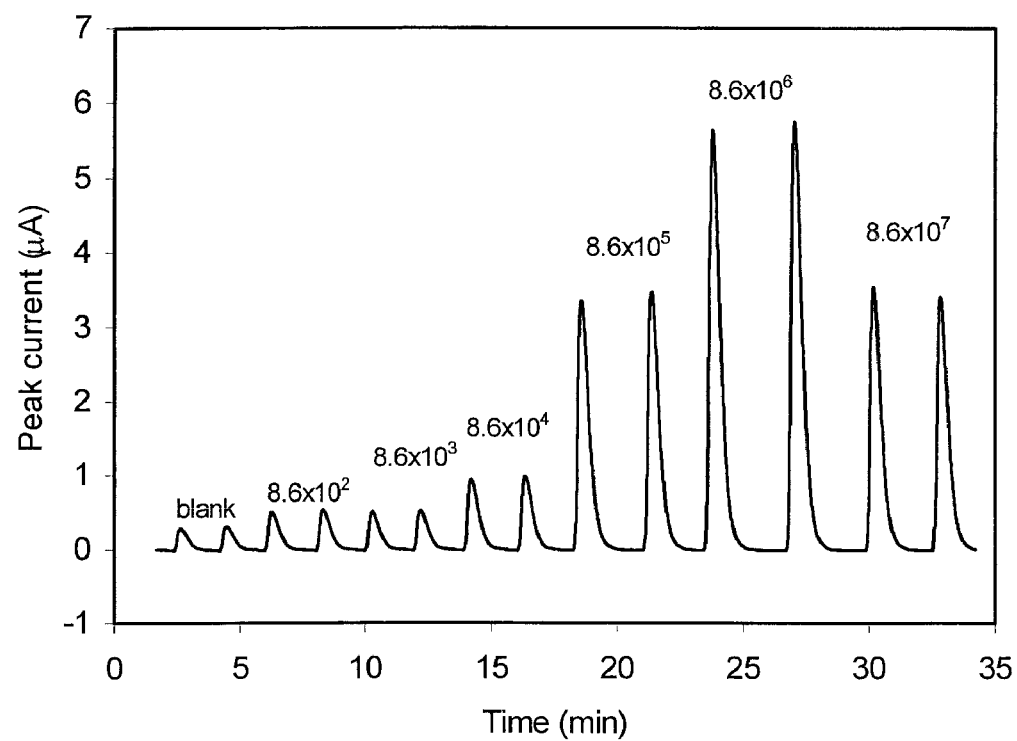
FIG. 7B shows electrochemical signals for samples containing S. Typhimurium from blank to $8.6 \times 10^7$ CFU/ml. (Two injections per signal were made for every concentration of the sample).
Figure 8A:
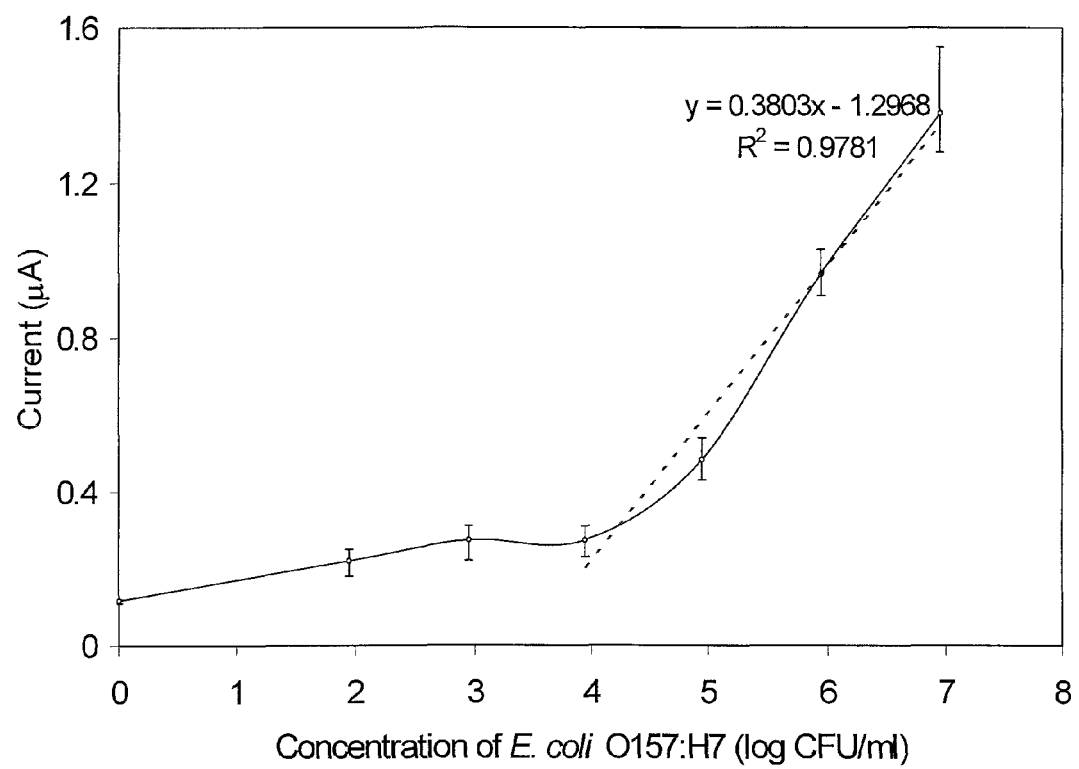
FIG. 8A is the calibration curve for the detection of *E. coli* O157:H7. Error bars represent standard deviations of three replicates.
Figure 8B:
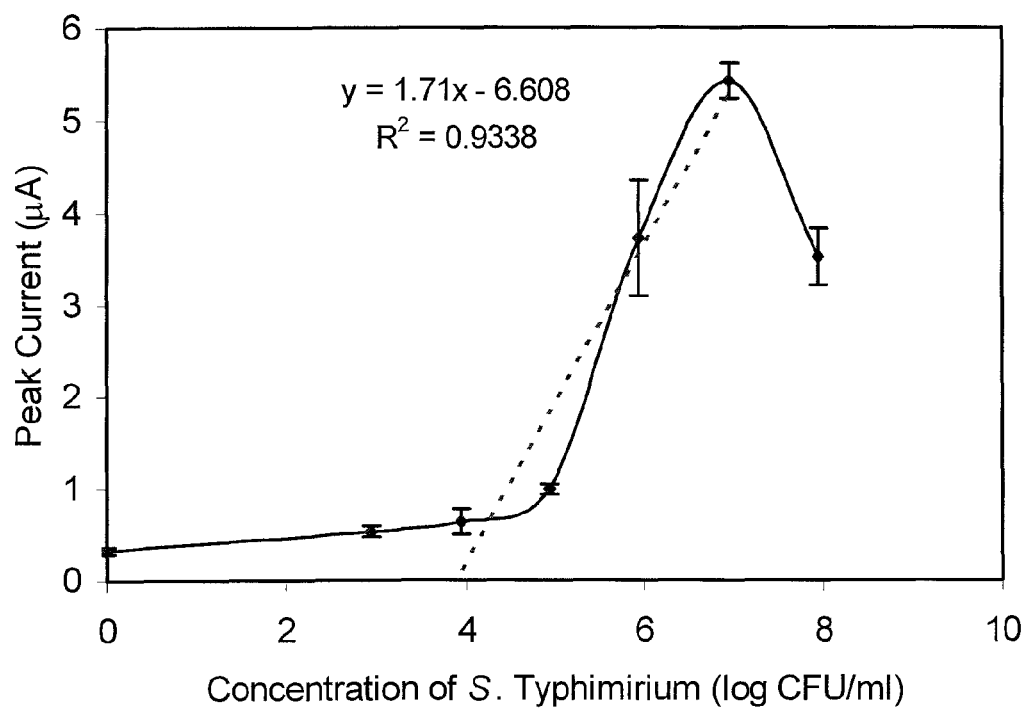
FIG. 8B is the calibration curve for the detection of S. Typhimurium. Error bars represent standard deviations of three replicates.

FIG. 7A and FIG. 7B are typical of electrochemical signals for the detection of E. coli O157:H7 from blank to $8.8\times10^6$ CFU/ml and S. Typhimurium from blank to $8.6\times10^7$ CFU/ml, respectively. FIG. 8A and FIG. 8B shows a calibration curve of electrochemical signals for samples containing E. coli O157:H7 from blank to $8.8\times10^6$ CFU/ml, and S. Typhimurium from blank to $8.6\times10^7$ CFU/ml, respectively. The signals for E. coli O157:H7 range from $8.8\times10^1$ to $8.8\times10^3$ CFU/ml. The signals of S. Typhimurium range from $8.6\times10^2$ to $8.6\times10^3$ CFU/ml and are not significantly different (p>0.05). When the concentration of E. coli O157:H7 is from $8.8\times10^1$ to $8.8\times10^3$ CFU/ml and the concentration of S. Typhimurium is from $8.6\times10^2\times8.6\times10^3$ CFU/ml, respectively, the signals only indicate the concentration range of the bacteria, and not the specific cell number.

A linear relationship between the peak current of phenol and logarithmic value of Salmonella is shown in FIG. 8B. Cell numbers ranged from $8.6\times10^3$ to $8.6\times10^6$ CFU/ml with an intercept of −6.608, a slope of 1.71 and a correlation coefficient of 0.966. However, the peak current decreased at very higher concentrations of S. Typhimurium (above $8.6\times10^7$ CFU/ml).

The nonlinearity at high bacterial concentrations may be explained by concentrations of the alkaline phosphatase labeled antibodies reacting with surplus bacteria, thus forming a competing reaction between "sandwich" antibodies-bacteria-alkaline phosphatase labeled antibodies and the complexes of alkaline phosphatase labeled antibodies-bacteria. Thus, complexes of alkaline phosphatase labeled antibodies-bacteria were removed by separation, and therefore the response decreased at higher concentrations of S. Typhimurium. This is in turn prevented the formation of the "sandwich" and it is often termed the "hook effect" (prozone phenomenon), which occurs in most types of enzyme immunoassays [P. M. Fratafico, et al., J. Clin. Microbiol. 33 (1995) 2188].

In addition, as the bacteria concentration increased, the number of enzymes present during the incubation increased. This may result in a substrate-limited enzyme reaction, thus reducing the peak current value. Adding more substrate might broaden the detection range, but may also increase the background noise. The cell numbers of Salmonella associated with processed food products usually is less than 1,000 CFU/ml, therefore, Salmonella titers ranging from $10^2$ to $10^6$ is a reasonable range in most investigations.

A significant difference (p<0.05) in the response between background control and samples containing $8.8\times10^1$ CFU/ml of E. coli O157:H7 was observed. No significant difference (p>0.05) was found for E. coli O157:H7 concentrations between $8.8\times10^1$ and $8.8\times10^3$ CFU/ml, indicating no linear relationship between the number of E. coli O157:H7 and the current response when the concentration of E. coli O157:H7 is less than $8.8\times10^3$ CFU/ml.

Compared to UV spectroscopy, electrochemistry provides a more sensitive detection method that is crucial to trace analysis [J. L. Mckillip, et al., J. Food Prot. 63 (2000) 855]. Using electrochemical detection we observed greater limits than those obtained using optical measurement [Y. Liu, et al., Anal. Chem. 73 (2001) 5180]. For E. coli O157:H7 the detection limit obtained may be as low as $8.8\times10^1$ CFU/ml, and the working range from $8.8\times10^1$ CFU/ml to $8.8\times10^6$ CFU/ml. For S. Typhimurium the detection limit obtained by electrochemical measurement was $8.6\times10^2$ CFU/ml, which is two orders of magnitude better than by absorption spectrophotometry. Even though absorption spectrophotometry is more convenient to use and much faster, electrochemical measurement remains the choice when attempting to detect lower concentrations of S. Typhimurium.

Antibody Specificity

The detection specificity of this method was investigated by comparing the detection results of samples containing individual isolates of E. coli O157:H7, L. monocytogenes, S. Seftenberg, S. Heidleberg, S. Typhimurium, samples containing the combinations of E. coli O157:H7, L. monocytogenes, and S. Typhimurium, and samples containing combinations of S. Typhimurium, S. Seftenberg, and S. Heidleberg.

Unlike the specificity for detection of E. coli O157:H7 that is detected with a monoclonal antibody, the anti-Salmonella antibody is a polyclonal antibody. As shown in Table 2, no significant difference ($p>0.05$) was observed between the background and signal of the samples containing only $5.0 \times 10^6$ CFU/ml of L. monocytogenes, $5.0 \times 10^6$ CFU/ml of E. coli O157:H7, or $5.0 \times 10^6$ CFU/ml of S. Heidleberg. This response may be due to the nonspecific binding by L. monocytogenes, E. coli O157:H7 or S. Heidleberg to the anti-Salmonella antibody. Similarly, the signals from the samples containing $5.0 \times 10^6$ S. Typhimurium and $5.0 \times 10^6$ S. Seftenberg were not significantly different ($p>0.05$).

TABLE 2

The specificity of the electrochemical biosensor for detection of Salmonella Typhimurium

| Samples | Concentration (CFU/ml) | Mean ± SD of peak current (µA) |
|---|---|---|
| S. Typhimurium background control | 0 (only PBS buffer) | 0.77 ± 0.057 |
| E. coli O157:H7 | $5.0 \times 10^6$ | 1.02 ± 0.076 |
| L. monocytogenes | $5.0 \times 10^6$ | 0.99 ± 0.012 |
| S. Heidleberg | $5.0 \times 10^6$ | 0.90 ± 0.100 |
| S. Typhimurium | $5.0 \times 10^6$ | 10.08 ± 0.036 |
| S. Seftenberg | $5.0 \times 10^6$ | 10.28 ± 0.076 |
| Mix 1[a] | $5.0 \times 10^6$ | 10.45 ± 0.050 |
| Mix 2[b] | $5.0 \times 10^6$ | 10.60 ± 0.050 |

[a]Mix 1 is the sample containing the same concentration ($5.0 \times 10^6$ CFU/ml) of S. Typhimurium, L. monocytogenes, and E. coli O157:H7.
[b]Mix 2 is the sample containing the same concentration ($5.0 \times 10^6$ CFU/ml) of S. Typhimurium, S. Seftenberg, and S. Heidleberg.

Figure 9:
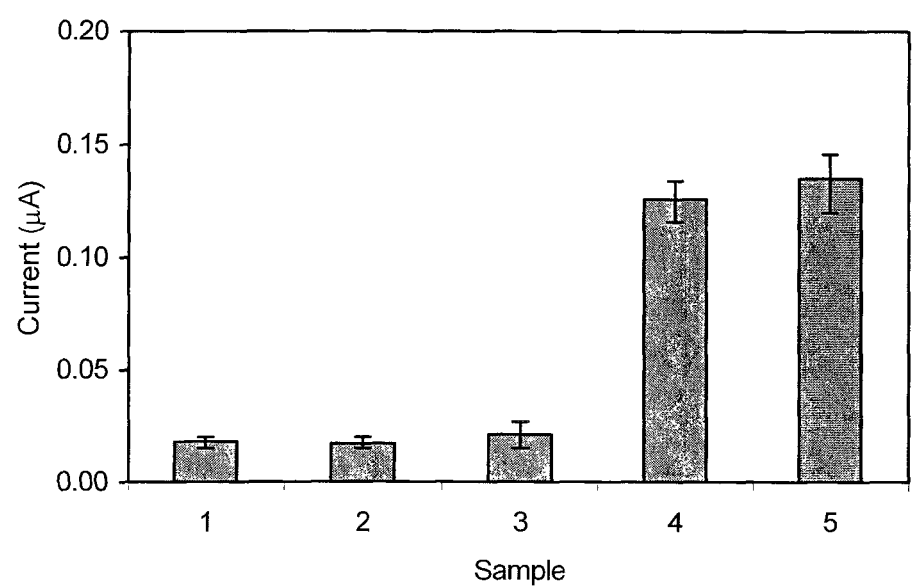
FIG. 9 shows selectivity of the system for a 0.5 ml sample at a 0.5 ml/h flow rate. Error bars represent standard deviations of three replicates. Sample 1: blank (0.5 ml pH 7.4 PBS buffer); Sample 2: 0.5 ml of $2.2 \times 10^5$ CFU/ml S. Typhimurium and $2.0 \times 10^5$ CFU/ml *L. monocytogenes*; Sample 3: 0.5 ml of $2.2 \times 10^6$ CFU/ml S. Typhimurium and $2.0 \times 10^6$ CFU/ml *L. monocytogenes*; Sample 4: 0.5 ml of $2.2 \times 10^5$ CFU/ml S. Typhimurium, $2.0 \times 10^5$ CFU/ml *L. monocytogenes* and $2.2 \times 10^5$ CFU/ml *E. coli* O157:H7.

Using the anti-E. coli O157:H7 antibody, selectivity was greatly increased among different bacteria. As shown in FIG. 9, the signal of the sample containing $2.2 \times 10^6$ CFU/ml S. Typhimurium and $2.0 \times 10^6$ CFU/ml L. monocytogenes were very similar to that of the blank, demonstrating that the anti-E. coli O157:H7 did not react with L. monocytogenes and S. Typhimurium. The signal from the sample containing $2.2 \times 10^5$ CFU/ml E. coli O157:H7 of the individual isolate, was not significantly different from the sample containing the combined isolates of E. coli O157:H7, $2.2 \times 10^5$ CFU/ml S. Typhimurium and $2.0 \times 10^5$ CFU/ml L. monocytogenes, thus indicating that L. monocytogenes and S. Typhimurium did not interfere the detection of E. coli O157:H7. Using the anti-E. coli O157:H7 antibody in the capillary column, detection of E. coli O157:H7 was not significantly affected by any non-specific binding by non-target bacteria.

Figure 10:
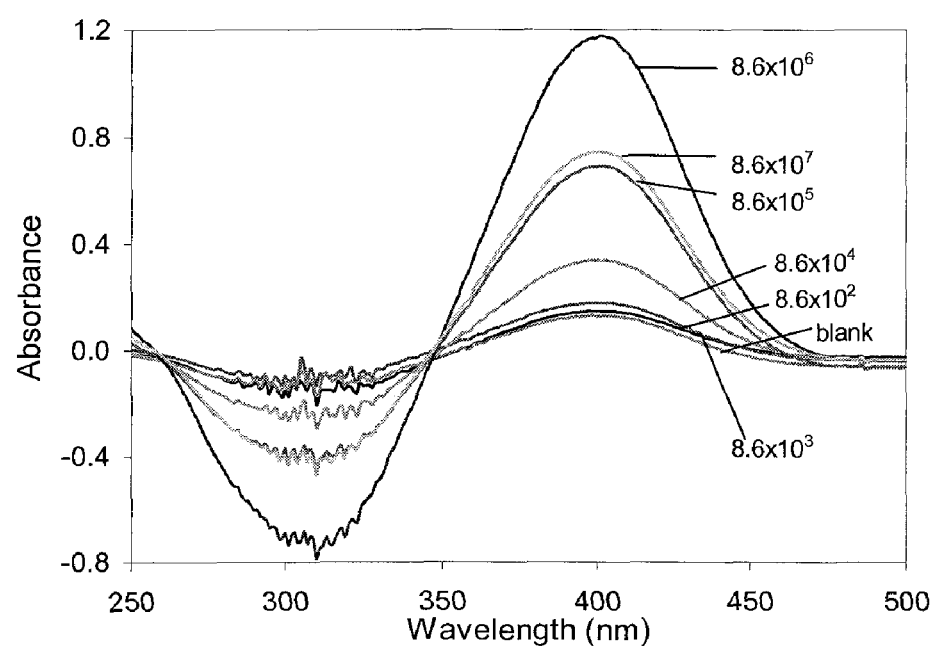
FIG. 10 shows the spectrum of absorbance for samples containing *E. coli* O157:H7 from blank to $8.8 \times 10^6$ CFU/ml.

FIG. 10 shows the original absorption spectrum for detection of S. Typhimurium samples. For S. Typhimurium the detection limit was $8.6 \times 10^4$ CFU/ml, and the working range was from $8.6 \times 10^4$ CFU/ml to $8.8 \times 10^6$ CFU/ml. A significant difference ($p<0.05$) was observed between background control and samples containing $8.6 \times 10^2$ CFU/ml of S. Typhimurium. However, the electrochemical response for S. Typhimurium at a concentration between $8.6 \times 10^2$ and $8.6 \times 10^3$ CFU/ml had no significant difference ($p>0.05$). There is not a linear relationship between the number of S. Typhimurium and the current response when the concentration of S. Typhimurium is less than $8.6 \times 10^3$ CFU/ml.

Detection of S. Typhimurium in Food Products

Figure 11:
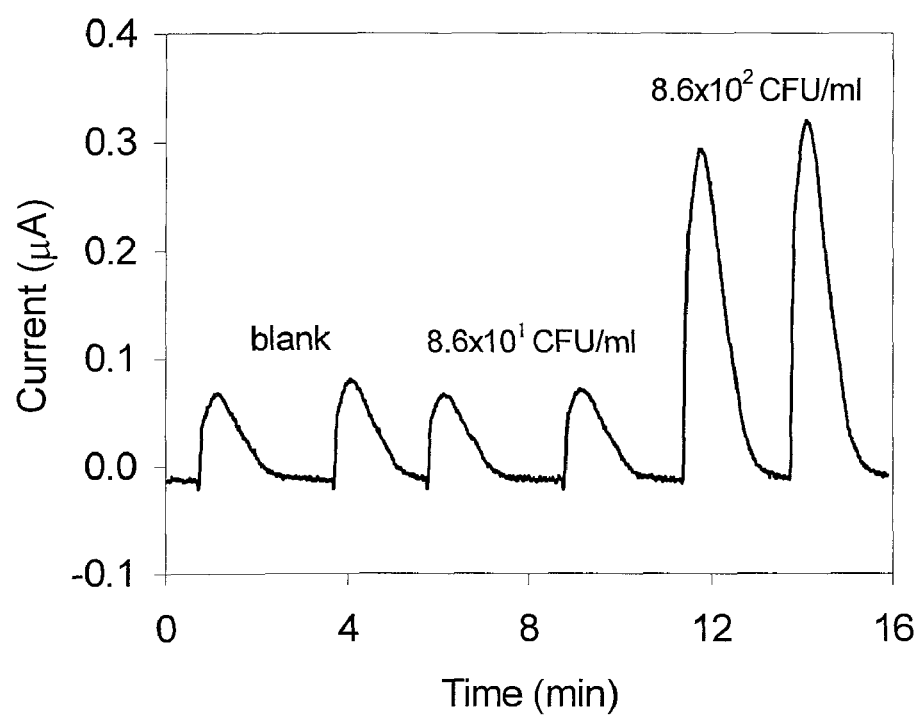
FIG. 11 shows the original data of electrochemical signals for milk samples containing S. Typhimurium from blank to $8.6 \times 10^3$ CFU/ml.

As shown in FIG. 11, S. Typhimurium was detected in milk samples. We observed that when 0.5 ml of milk as the background control and 0.5 ml of inoculated S. Typhimurium in milk were pumped into the columns, the result indicates that as low as $8.6 \times 10^2$ CFU/ml of S. Typhimurium inoculated in milk could be detected without any enrichment. Statistical analysis of the data indicate that the responses were significantly different ($p<0.05$) between the background control and milk with S. Typhimurium at a concentrations of $8.8 \times 10^2$ CFU/ml.

EXAMPLES

Example 1

Antibodies

Anti-E. coli O157:H7 antibodies (1 mg) and alkaline phosphatase-labeled affinity purified antibodies to E. coli O157:H7 (0.1 mg), purchased from Kirkegaard & Perry Laboratories (Gaithersburg, Md.), were rehydrated with 1 ml of 50% glycerin water solution. Dilution of 1:10 of the antibodies and 1:100 of the alkaline phosphatase-labeled antibodies were prepared before use.

Primary and secondary antibodies, anti-Salmonella antibodies and alkaline phosphatase-labeled affinity purified anti-Salmonella antibodies, were obtained from Kirkegaard & Perry Laboratories (Gaithersburg, Md.). One mg of anti-Salmonella antibodies and 0.1 mg of alkaline phosphatase-labeled affinity purified anti-Salmonella antibodies were rehydrated with 1 ml of 50% glycerin water solution to obtain 1:10 and 1:100 dilutions, respectively.

Tyrosinase (EC 1.14. 18. 1, from mushroom, 3000 units/mg), bovine serum albumin (BSA), horseradish peroxidase (EC 1. 11.1. 7, type II, 240 units/mg), tris (hydroxymethyl) aminomethane (Tris, 99.9%), pH 7.4 phosphate buffer saline (PBS), and pH 7.4, 1% BSA were purchased from Sigma (St. Louis, Mo.). Glutaric dialdehyde (50 wt. % solution in water), 3-aminopropyltrimethoxysilane (97%), hydrogen peroxide (30 wt. %), phenol (99%), phenyl phosphate disodium (98%) and acetonitrile were obtained from Aldrich (Milwaukee, Wis.). $Na_2HPO_4$, $NaH_2PO_4 \cdot H_2O$ and $MgCl_2$ were purchased from Fisher (Pittsburgh, Pa.). Fused-silica capillary columns (100, 150, and 250 µm i.d.) were from Polymicro Technologies (Phoenix, Ariz.). Other chemicals were of analytical grade and were used without further purification.

A stock solution of 0.1 M phenol was prepared by dissolving an appropriate amount of phenol in acetonitrile and stored at 4° C. Standard phenol was diluted in PBS (pH 6.9) on the day of use from the stock solution. A stock solution of 0.1 M hydrogen peroxide was prepared in water and stored at 4° C.

Example 2

Bacteria and Culture Plating Methods

Escherichia coli O157:H7 (ATCC 43888) as a target pathogen and Salmonella Typhimurium (ATCC 14028) and Listeria monocytogenes (FDA 10143) as competing bacteria were obtained from American Type Culture Collection (Rockville, Md.). The pure culture of *E. coli* O157:H7, *S.* Typhimurium, and *L. monocytogenes* were grown in brain heart infusion (BHI) broth (Remel, Lenexa, Kans.) at 37° C. for 20 hours before use. The culture was serially diluted to $10^{-8}$ with physiological saline solution (PSS) and viable cell number was determined by plate count. Microbial tests for *E. coli* O157:H7 was performed by surface plating 0.1 ml of dilutions on MacConkey sorbitol agar (remel, Lenexa, Kans.). After incubation at 37° C. for 24 hours, *E. coli* O157:H7 colonies on the plate were counted to determine the number of colony forming units per ml (CFU/ml). Cell numbers of S. Typhimurium and *L. monocytogenes* in pure culture were determined by the same method with the exception of the use of xylose lysine tergitol agar ($XLT_4$) (remel, Lenexa, Kans.) and Oxoid agar (Oxoid LTD, Basingstoke Hampshire, U.K.), respectively.

Alternatively, pure culture of S. Typhimurium (ATCC 14028) as a target pathogen, *Escherichia coli* O157:H7 (ATCC 43888), *Salmonella* Seftenberg (ATCC 46845) and *Salmonella* Heidleberg (8326) as competing bacteria were obtained from American Type Culture Collection (Rockville, Md.). *Listeria monocytogenes* (FDA 10143), as a competing bacteria, was obtained from the Food and Drug Administration. All cultures were grown in brain heart infusion (BHI) broth (remel, Lenexa, Kans.) at 37° C. for 20 hours before use. The culture was serially diluted to $10^{-8}$ with physiological saline solution (PSS) and viable cell number was determined by plate count. S. Typhimurium, S. Seftenberg and S. Heidleberg culture counting was performed by surface plating 0.1 ml of dilutions on xylose lysine tergitol agar ($XLT_4$) (remel, Lenexa, Kans.). After incubation at 37° C. for 24 hours, the colonies on the plate were counted to determine the number of colony forming units per ml (CFU/ml). The cell numbers of *E. coli* O157:H7 and *L. monocytogenes* were determined by the same method with the exception of the use of MacConkey sorbitol agar (remel, Lenexa, Kans.) and Oxoid agar (Oxoid LTD, Basingstoke Hampshire U.K.), respectively.

Example 3

Capillary Column Modification and Antibody Immobilization

The desired antibody was immobilized onto the inner wall of columns basically according the method described by Liu and Li [Y. Liu, Y. Li, Anal. Chem. 73 (2001) 5180]. Using a series of syringes on a Harvard PHD 2000 advanced syringe pump (Harvard Apparatus, Holliston, Mass.), a series of fused-silica capillary columns (3 m) were treated with 1 M NaOH and 1M HCl, and dried out overnight. Dried capillary columns were treated with 3-aminopropyltrimethoxysilane (1% methanol solution), incubated for 70° C. for 4 hours to allow the formation of the aminopropyl derivative of glass, rinsed with methanol, dried overnight, reacted with glutaraldehyde, and washed with PBS (pH=7.4) solution. Our study showed that the concentration of antibodies had great effect on the detection limit. Therefore, 0.1 mg/ml concentration of the antibody was used in order to decrease the detection limit. For *E. coli* detection, 0.4 ml of anti-*E. coli* O157:H7 antibodies (0.1 mg/ml) was pumped into each of the columns for coupling, and followed by washing with PBS (pH=7.4) solution. These anti-*E. coli* antibody modified columns were cut into 25 cm long pieces and put into a refrigerator at 4° C. for later use. For *Salmonella* detection, anti-*Salmonella* antibodies (0.1 mg/ml) were pumped into prepared columns for coupling, and followed by washing columns with PBS (pH=7.4) solution. These anti-Salmonella antibody modified columns were cut to 40 cm long pieces and put into a refrigerator at 4° C. for later use.

Example 4

Immuno-Separation and Enzymatic Reaction in the Modified Capillary Column for the Detection of *E. coli* O157:H7

The 0.5 ml of *E. coli* O157:H7 sample and 50 µl of alkaline phosphatase-labeled affinity purified antibodies (1 mg/l) were pumped into the column (length=25 cm) at a flow rate of 0.5 ml/h to form the sandwich immunocomplexes on the inner wall of the column. The column was then rinsed with 2×1 ml of PBS (0.01 M, pH 7.4, 1% BSA) and 1 ml of Tris buffer (0.1 M, pH 8.0). The substrate, composed of $1.0 \times 10^{-3}$ M phenyl phosphate disodium and $1.0 \times 10^{-2}$ M $MgCl_2$ in pH 9.0, 0.1 M Tris buffer, was pumped through the column at a flow rate of 2 ml/h. The product of the enzymatic reaction from the bioreactor was collected at the outlet. After the enzymatic reaction, 10 µl of 0.1 M $H_2O_2$ was added to the solution to amplify the electrochemical signal of the phenol generated, which was then determined by the bienzyme biosensor in a flow injection system.

Procedures for fabrication of tyrosinase-horseradish peroxidase electrodes were described in detail in the report by Ruan and Li [C. Ruan, Y. Li, Talanta 54 (2000) 1095]. Dual glassy carbon electrodes (BAS, West Lafayette, Ind.) were polished and sonicated, washed with deionized water and dried in the air. Two mg tyrosinase, 2 mg horseradish peroxidase and 100 µg bovine serum albumin were separately dissolved in 100 µl, 0.05 M phosphate buffer solution (PBS, pH 7.0, without KCl). Forty µl of the above dissolved tyrosinase solution, 10 µl of the above dissolved horseradish peroxidase solution, 10 µl of BSA and 10 µl of 5% glutaric dialdehyde and 20 µl of PBS (pH 7.0, without KCl) were mixed thoroughly. A 2.5 µl of the resulting mixture was spread on the surface of a glassy carbon disk electrode (3 mm diameter). All modified enzyme electrodes were dried overnight at 4° C. and washed with deionized water before use.

For the electrochemical measurement using a bienzyme electrode, a flow injection analysis (FIA) system connected with an electrochemical cell was used for the detection of phenol production. The bienzyme electrode was inserted into a cross-flow thin-layer amperometric cell comprising an Ag/AgCl (3.0 M NaCl) reference electrode and a stainless steel auxiliary electrode (BAS, West Lafayette, Ind.). The amperometric cell was connected to a single channel flow injection system consisting of a six ports injection valve (Rheodyne, Berkley, Calif.) with a 100 µl injection loop, to an electrochemical detector (model 800, CH Instruments, Dallas, Tex.). An HP1100 series isocratic pump (Hewlett-Packard, Waldbronn, Germany) was used to drive the carrier solution at a rate of 1.0 ml/min. All measurements were performed at an applied potential of −0.2 V (vs. Ag/AgCl). A 0.05 M, pH 7.0 PBS was used throughout the tests as a carrier solution in the FIA system.

Before all electrochemical measurements, each electrode was potentiostated at the working potential, allowing the background current to decay to a steady state value. The electrode was activated for 5 min using a solution of $10^{-5}$ M standard phenol (containing $10^{-3}$ M $H_2O_2$).

Example 5

Immuno-Separation and Enzymatic Reaction in the Modified Capillary Column for the Detection of S. Typhimurium The 0.5 ml of S. Typhimurium sample and 100 µl of alkaline phosphatase-labeled affinity purified antibodies (2 mg/l) were pumped into the columns (length=40 cm) to form the sandwich immunocomplex on the inner wall of the columns under the temperature of 37° C. The columns were then rinsed with 2×1 ml of PBS (0.01 M, pH 7.4, 1% BSA) and 1 ml of Tris buffer (0.1 M, pH 8.0). The electrochemical substrate, composed of $1.0 \times 10^{-3}$ M phenyl phosphate disodium and $1.0 \times 10^{-2}$ M $MgCl_2$ in 1.0 M, pH 10.0 Tris buffer, or optical substrate, composed of $2.0 \times 10^{-4}$ M 4-nitrophenyl phosphate and $1.0 \times 10^{-2}$ M $MgCl_2$ in 1.0 M pH 9.0 Tris buffer, was pumped through the columns. The product of the enzymatic reaction from the capillary bioreactor was collected at the outlet. After the enzymatic reaction, for electrochemical measurement, a flow injection analysis (FIA) system connected with an electrochemical cell was used for the detection of phenol production. The bienzyme electrode was inserted into a cross-flow thin-layer amperometric cell comprising an Ag/AgCl (3.0 M NaCl) reference electrode and a stainless steel auxiliary electrode (BAS, West Lafayette, Ind.). The amperometric cell was connected to a single channel flow injection system consisting of a six ports injection valve (Rheodyne, Berkley, Calif.) with a 100 µl injection loop, to an electrochemical detector (Model 800, CH Instruments, Dallas, Tex.). An HP1100 series isocratic pump (Hewlett-Packard, Waldbronn, Germany) was used to drive the carrier solution at a rate of 0.5 ml/min. All measurements were performed at an applied potential of −0.2 V (vs. Ag/AgCl). A 0.05 M, pH 7.0 PBS was used throughout the tests as a carrier solution in the FIA system. Before all electrochemical measurements, each electrode was potentiostated at the working potential, allowing the background current to decay to a steady state value. The electrode was activated for 5 min using a solution of $10^{-5}$ M standard phenol (containing $10^{-3}$ M $H_2O_2$). 10 µl of 0.1 M $H_2O_2$ was added to the solution to amplify the electrochemical signal of the phenol generated, which was then determined by the bienzyme biosensor in a flow injection system.

For optical measurement, the product of 4-nitrophenol was detected by measuring the absorbance at 400 nm using a spectrophotometer (HP 8453 UV-Visible Spectrophotometer, Agilent Technologies, Palo Alto, Calif.).

Example 6

Statistical Analysis

For *E. coli* measurements, the difference between the background and sample responses was analyzed using t test. For the detection of S. Typhimurium the means and standard deviations of electrochemical and optical signals were calculated, and the difference between the background response and the response of samples was analyzed using t test. Statistical analysis for both setups was performed using the JMP program (SAS Institute Inc., Cary, N.C.).

Example 7

Food Sample Preparation

Milk was purchased from a local grocery store. 0.2 ml of diluted S. Typhimurium pure culture (ranging from $8.6 \times 10^2$ to $8.8 \times 10^7$ CFU/ml) was added to 1.8 ml milk to get the final inoculation concentration ranging from $8.8 \times 10^1$ to $8.8 \times 10^6$ CFU/ml. 0.5 ml of milk without bacteria was used as the background control.

What is claimed is:

1. A method for detecting a microorganism comprising:
   immobilizing an antibody to a capillary column;
   flowing a first solution containing at least one antigen through the entire length of the capillary column one time, wherein the antigen is associated with a microorganism and the antigen is capable of binding the antibody, and wherein the volume of the first solution flowed through the capillary column exceeds the volume of the capillary column;
   flowing a second solution containing an antigen marker agent labeled with an enzyme a through the entire length of said capillary column, wherein the antigen marker agent will bind to said antigen;
   flowing a third solution containing a substrate of the enzyme to generate an enzymatic product through said capillary column; and
   measuring a concentration of said enzymatic product to determine a number of microorganisms in the first solution.

2. The method of claim 1, wherein said antibody is a monoclonal or a polyclonal antibody.

3. The method of claim 1, wherein said antibody is a fragment antigen binding (Fab) fragment.

4. The method of claim 1, wherein said antibody is an antibody derivative that retains antigen binding activity.

5. The method of claim 1, wherein said antibody is an anti-*E. coli* 0157: H7 antibody or an anti-*Salmonella* antibody.

6. The method of claim 1, wherein said capillary column inner diameter is between 90 and 550 micrometers and the capillary column length is between 20 and 50 centimeters.

7. The method of claim 1, wherein said microorganism is a virus, bacteria, fungi, or parasite.

8. The method of claim 7, wherein said microorganism is a pathogenic toxin producing bacteria.

9. The method of claim 8, wherein said pathogenic toxin producing bacteria is *Escherichia* or *Salmonella*.

10. The method of claim 1, wherein said measuring is by optical detection or by electrochemical detection.

11. The method of claim 10, wherein said optical detection is UV absorbance or fluorescence.

12. The method of claim 10, wherein said electrochemical detection is an electrochemical enzyme biosensor.

13. The method of claim 1, wherein the rate of flowing the first solution is between about 0.5 ml/hr and about 2.0 ml/hr.

14. The method of claim 1, wherein the linear flow velocity is about 10 ml/hr $mm^2$.

15. A method for detecting a microorganism comprising:
   immobilizing an antibody to a capillary column;
   flowing a first solution containing at least one antigen through the entire length of the capillary column without reflowing, wherein the antigen is associated with a microorganism and the antigen is capable of binding the antibody, and wherein the volume of the first solution flowed through the capillary column exceeds the volume of the capillary column;
   flowing a second solution containing an antigen marker agent labeled with an enzyme through the entire length of said capillary column, wherein the antigen marker agent will bind to said antigen;

flowing a third solution containing a substrate of the enzyme to generate an enzymatic product through said capillary column; and measuring a concentration of said enzymatic product to determine a number of microorganisms in the first solution.

16. The method of claim 15, wherein said capillary column inner diameter is between 90 and 550 micrometers and the capillary column length is between 20 and 50 centimeters, and wherein the rate of flowing the first solution is between about 0.5 ml/hr and about 2.0 ml/hr.

17. The method of claim 15, wherein the linear flow velocity is about 10 ml/hr mm$^2$.

18. A method for detecting a microorganism comprising:
immobilizing an a antibody to a capillary column;

flowing a first solution containing at least one antigen through the entire length of the capillary column without reflowing, wherein the antigen is associated with a microorganism and the antigen is capable of binding the antibody, and wherein the volume of the first solution flowed through the capillary column exceeds the volume of the capillary column;

flowing a second solution containing an antigen marker agent labeled with a nanocrystal through the entire length of said capillary column, wherein the antigen marker agent will bind to said antigen; and measuring a concentration of the nanocrystal hound to the capillary column to determine a number of microorganisms in the first solution.

19. The method of claim 18, wherein said capillary column inner diameter is between 90 and 550 micrometers and the capillary column length is between 20 and 50 centimeters, and wherein the rate of flowing the first solution is between about 0.5 ml/hr and about 2.0 ml/hr.

20. The method of claim 18, wherein the linear flow velocity is about 10 ml/hr mm$^2$.

* * * * *